US006063579A

United States Patent [19]

Bevirt et al.

[11] Patent Number: 6,063,579

[45] Date of Patent: May 16, 2000

[54] ALIGNMENT MECHANISM

[75] Inventors: Joeben Bevirt, Emerald Hills; Gabriel Brinton, Palo Alto; Eric Lachenmeier, Los Altos, all of Calif.

[73] Assignee: Incyte Pharmaceuticals, Inc., Palo Alto, Calif.

[21] Appl. No.: 09/183,776

[22] Filed: Oct. 30, 1998

[51] Int. Cl.[7] ................................ C12Q 1/68; B01L 3/00

[52] U.S. Cl. ................................................ 435/6; 422/99

[58] Field of Search ......................... 435/6, 288.4, 288.3; 422/99, 100, 101, 104

[56] References Cited

U.S. PATENT DOCUMENTS 5,497,670 3/1996 Carl ..................................... 73/863.32

5,851,492 12/1998 Blattner .................................. 422/102

*Primary Examiner*—Eggerton A. Campbell

*Assistant Examiner*—Jeffrey S Lundgren

*Attorney, Agent, or Firm*—Incyte Pharmaceuticals, Inc; Karen Guerrero; Narinder Banait

[57] ABSTRACT

The invention is a method for improving material transfer manipulations in an automated format. The method entails deforming the work surface of a plate to flatten or elongate the work surface prior to or simultaneously to material transfer.

12 Claims, 4 Drawing Sheets

ALIGNMENT MECHANISM

FIELD OF THE INVENTION

The present invention relates to a novel alignment mechanism. More particularly, the invention relates to a method for precisely positioning a work surface to facilitate the transfer of materials in an automated format.

BACKGROUND OF THE INVENTION

A microtiter plate, or any other piece of laboratory equipment, may be subject to multiple rounds of heating and cooling during a series of manipulations. As a result of the thermal cycling, the plate may become nonuniform in the flatness of its working surface causing the depth of individual wells to vary. The nonuniformity of the plate may then prevent the automation of material transfer processes. For example, the dispenser may be too far from the bottom of the well for efficient material transfer. In other cases, the dispenser may be too close to the well bottom pressing against the well bottom and blocking material transfer.

The present invention overcomes the above-described problem during material transfer processes by providing a method for flattening or elongating a work surface in order to precisely align the work surface in relationship with a dispenser.

SUMMARY OF THE INVENTION

In one aspect, the present invention relates to a method for improving material transfer to and from discrete locations on a work surface of a plate. The method comprises the steps of (a) deforming the work surface of the plate to generate a deformed work surface and (b) transferring material to or from the deformed work surface, whereby the deformed work surface provides improved material transfer. The deforming step may entail flattening the work surface of the plate, elongating the work surface of the plate, or a combination of both processes. As a consequence of the deforming step, the plate is precisely positioned with respect to one or more material dispensers. The deforming step may be accomplished by the application of pressure. The pressure may be a positive pressure applied to the work surface of the plate or a vacuum pressure applied to the plate opposite the work surface.

In one embodiment, the plate is deformed by compressing the plate against a mold comprising (a) a bottom surface, (b) a peripheral wall having a substantially planar upper surface and an elastomeric seal positioned at said upper surface, said peripheral wall positioned to contact a portion of the plate, preferably the outer rim of the plate. The seal has the necessary flexibility to allow for horizontal or vertical motion of the plate with respect to the mold when pressure is applied for flattening the plate against the mold. The mold may also contain one or more internal structures for centrally positioning the plate with respect to the mold prior to and during the application of pressure. Preferably, vacuum pressure is applied.

The method of the invention may be employed in an automated assay format, wherein material is transferred to and from discrete locations on the work surface of a plurality of plates. The work surface of a first plate is deformed to generate a deformed work surface so that the deformed work surface provides improved material transfer Then materials are transferred to or from the deformed work surface. The first plate may be released from the mold and replaced by one or more additional plates, as desired.

DESCRIPTION OF THE INVENTION

The present invention provides a method for improving material transfer to discrete locations on the work surface of one or more plates. A work surface is any surface where a manipulation may be performed. The work surface may have a variety of discrete locations, such as wells, trenches, channels, pores, and the like. The method involves deforming the work surface of a plate prior to or simultaneous to a material transfer step. In this manner, any nonuniformity of the work surface of the plate is minimized and the transfer of materials to and from the plate in an automated format can be made more consistent and complete. The deforming step comprises flattening or elongating the work surface of the plate. Preferably, the flattening or elongating entails applying pressure. Pressure may be applied by exerting a positive force on the work surface of the plate. Alternatively, pressure may be applied by exerting vacuum pressure on the plate opposite the work surface of the plate.

In one embodiment, the plate is compressed against a mold to flatten or elongate the work surface of the plate. A key feature is that the mold includes an elastomeric seal that contacts the assay plate and which is sufficiently flexible or deformable to allow for horizontal or vertical motion of the plate with respect to the mold when pressure is applied. Pressure may be applied by exerting a positive force on the work surface of plate, preferably along that portion of the plate that contacts the elastomeric seal. Alternatively, pressure may be applied by exerting vacuum pressure on the plate opposite the work surface of the plate. Again, pressure is preferably applied where the plate contacts the elastomeric seal. Typically, contact is made between the plate and the elastomeric seal at the outer rim of the plate. The mold also includes one or more internal structures for centrally positioning the plate prior to and during the application of pressure. In this manner, an assay plate is held from the center of the mold while the outer rim of the assay plate is moved horizontally or vertically to flatten the assay plate against the mold when pressure is applied.

Figure 1:
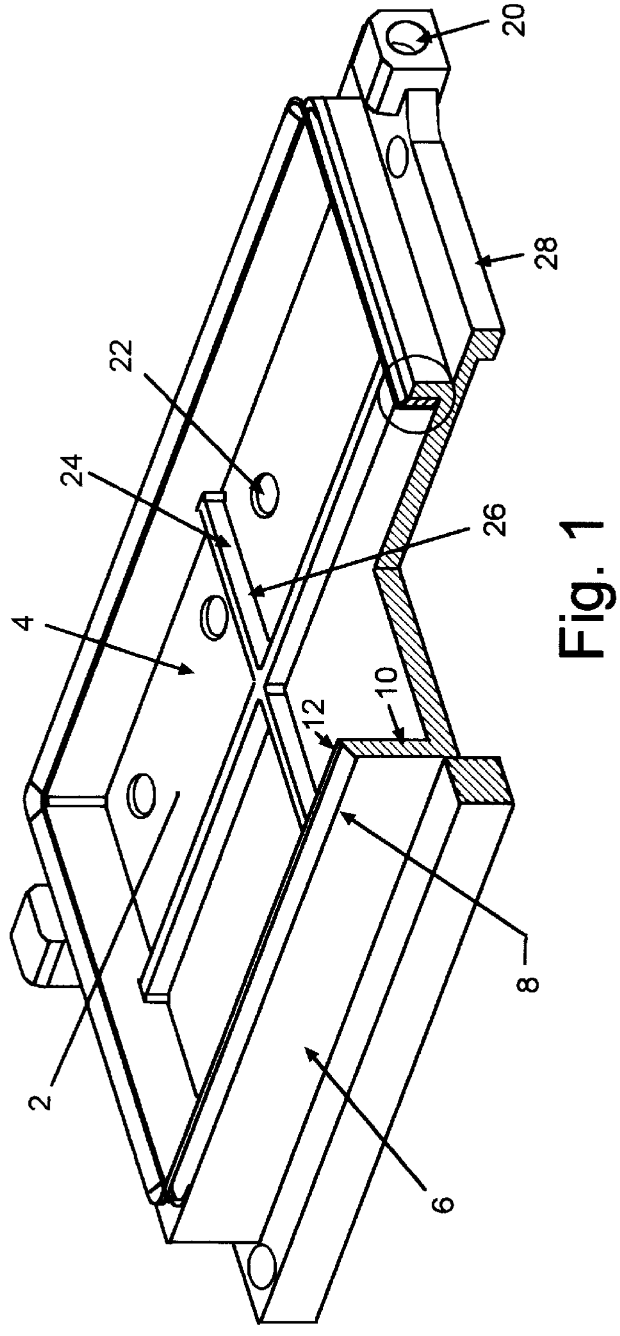
FIG. 1 is a perspective view of an embodiment of the mold in which an elastomeric seal is positioned in a groove contained within the peripheral wall of the mold.
Figure 2:
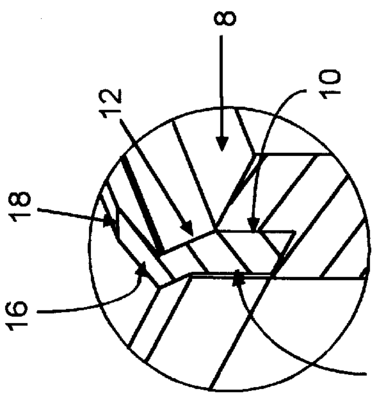
FIG. 2 is a close-up view of the embodiment of the mold of FIG. 1.

The drawings illustrate preferred embodiments of the mold for use in the method of the present invention. As shown in FIG. 1, the mold 2 comprises a bottom surface 4. A peripheral wall, such as peripheral wall 6, defines a portion of the bottom surface that is enclosed by the wall. The peripheral wall as shown in FIG. 1, and shown in greater detail in FIG. 2, has a substantially planar upper surface 8 and a groove 10 contained therein. Removably positioned in the groove, is an elastomeric seal 12. The elastomeric seal may have a distorted Z-shaped structure in vertical cross-section. As illustrated in FIG. 2, the bottom portion 14 is contained within the groove and a top portion 16 extends out of the groove and is tapered to be narrowest at its mold-distal end 18.

As shown in FIG. 1, the mold contains means for applying pressure. The mold contains one or more vacuum ports, such a vacuum port 20, which can be releasably connected to a vacuum source via an automatically or manually controlled valve. A particular vacuum port is in airtight communication with one or more vacuum outlets, such as outlet 22, so as to remove air from the bottom surface area. Additionally, the mold has one or more internal structures, such as internal structure 24, for centrally positioning a plate with respect to said mold before and when pressure is applied to flatten the plate against the mold. In the preferred embodiment, the internal structure consists of at least two perpendicular strips, such as strip 26, having a sufficient width to fit snugly between two rows of assay plate wells.

FIG. 1 also shows some additional features of the mold. For example, the mold may contain a locking base 28 for stably and/or movably positioning the mold in a position for pulling a vacuum or for automated assay manipulations. The mold may be prepared from any rigid structural material.

Figure 3:
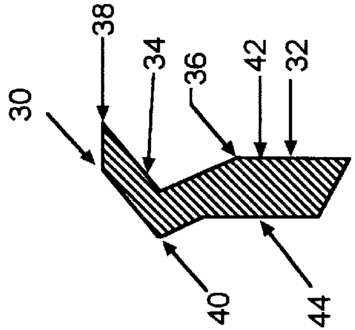
FIG. 3 is a cross-sectional view of the elastomeric seal of FIG. 1.

Now focusing on one embodiment of the elastomeric seal, as illustrated in cross-section at FIG. 3. The elastomeric seal 30 typically has a distorted Z-shape and comprises a bottom portion 32 and a top portion 34. The bottom portion is typically of rectangular dimensions. The top portion is tapered so that the mold-proximal end 36 is of approximately the same width as the bottom portion whereas the mold-distal end 38 is narrower than the bottom portion. The top portion also contains a V-shaped corner 40 at an intermediate location between proximal and distal ends. The elastomeric seal has outer 42 and inner 44 surfaces. The angle of the outer surface from end 36 to corner 40 may vary from 30 to 40° and the angle of the inner surface may vary from 30 to 50°. Preferably, the angle of the outer surface from end 36 to corner 40 is 38° and the angle of the inner surface is 48°. The angle of the outer surface from corner 40 to end 38 may vary from 45 to 60° and that of the inner surface may vary from 35 to 50°. Preferably, the angle of the outer surface from corner 40 to end 38 is 47° and that of the inner surface is 42°.

The dimensions of the bottom portion may vary in width to achieve the degree of flexibility that is desired, and may be of any length depending on the length of the groove or on the extent that it is desired that the bottom portion extend out of the groove. Preferably, the length is 0.150 cm. The top portion may rise to any extent desired, but preferably from 0.05 to 0.12 cm above end 36, more preferably from 0.6 to 0.11 cm above end 36. Preferably, the width of the distal end is between 0.015 to 0.035 cm, more preferably 0.02 to 0.03 cm. On the outer surface side, the distal end of the top portion may extend outwards from the bottom portion surface. Alternatively, the distal end may not extend beyond the bottom portion surface. Typically, the inner surface side of the V-shaped corner extends from between 0.025 to 0.045 cm, more preferably between 0.030 to 0.035 cm inwards from the bottom portion inner surface. The V-shaped corner may be oriented away from the center of the mold or toward the center of the mold, as illustrated.

Generally, the elastomeric seal is prepared from any elastomeric material by any of a plurality of molding processes known to those skilled in the art, such as an injection molding process or the like. Preferably, the elastomeric material is a material with a Shore A Durometer value of between about 20 to 70, preferably about 30 to 60, and most preferably about 40. Examples of such materials may be prepared from commercially available monomers/polymers and include natural latex rubber, Butyl (such as Exxon Butyl available from Exxon Chemicals Co., Houston, Tex.), ethylene propylene diene monomer (EPDM) (Nordel available from Dupont Dow Elastomers, Wilmington, Del.), Hypalon (chlorosulfonated polyethylene available from Dupont Dow Elastomers), Neoprene (available from Dupont Dow Elastomers), Nitrile (Buna-N) (Chemigum available from Goodyear Tire and Rubber Co.), polyurethanes (such as Adiprene and Vibrathane available from Uniroyal Chemical Co., Middlebury, Conn.), silicones (such as P-125, a room temperature vulcanizing (RTV) silicone available from Silicones Inc., High Point, N.C.), Sorbothane (available from Sorbothane Inc., Kent, Ohio), SBR (available from Goodyear Tire and Rubber Co.), Viton (available from Dupont Dow Elastomers), and the like.

Figure 4:
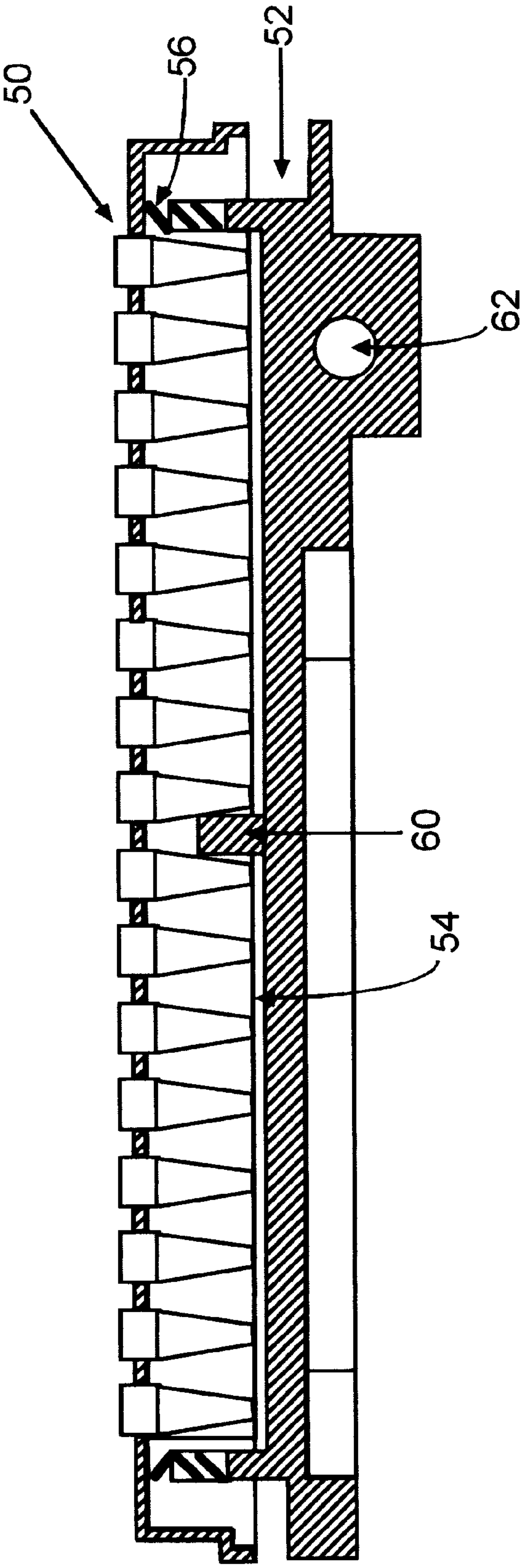
FIG. 4 is a cross-sectional view of a 384 well microtiter plate supported by a mold prior to application of pressure.
Figure 5:
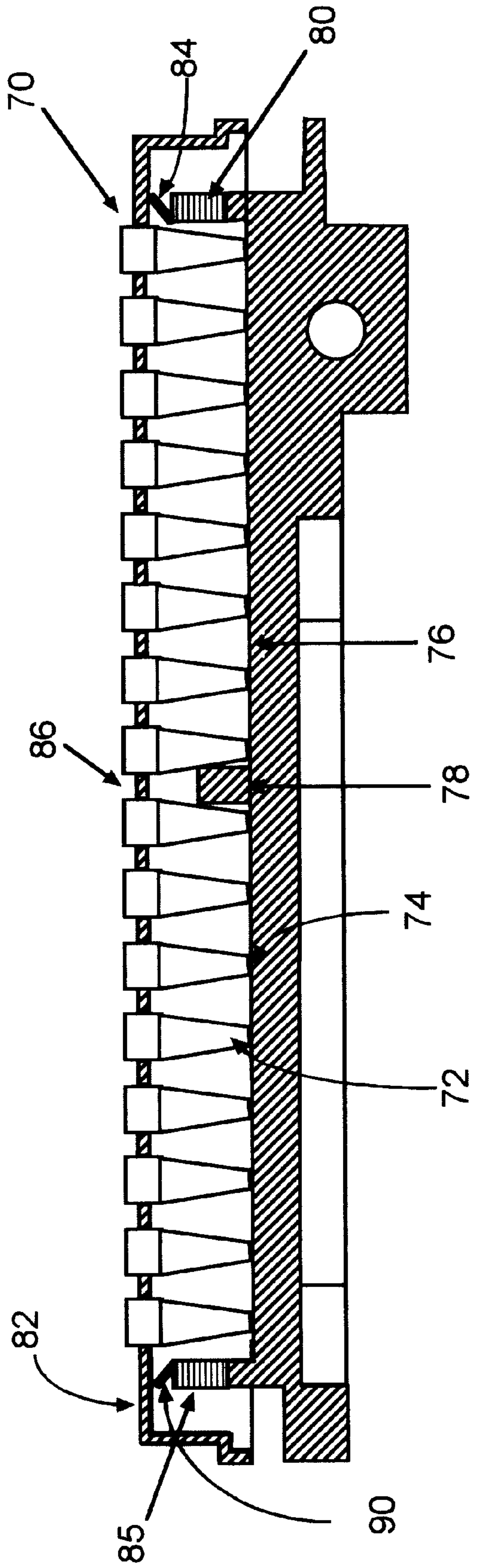
FIG. 5 is a cross-sectional view of a 384-well microtiter plate supported by a mold during the application of pressure.

In the method of the invention, and as illustrated in FIG. 4 in cross-section, a plate, such as a 384-well microtiter plate 50, is placed on mold 52. The Figure shows the positioning of the microtiter plate prior to applying pressure. The microtiter plate is shown elevated from the bottom surface 54 of the mold and supported by the top portion 56 of the elastomeric seal 58. Internal structure 60 is used to correctly position the microtiter plate with respect to the structure prior and during the application of a vacuum. The Figure further shows a vacuum channel 62 leading from the vacuum port to individual vacuum outlets FIG. 5 illustrates in cross-section how the plate may be deformed to flatten the work surface of the assay plate once pressure is applied. Microtiter plate 70 has a plurality of wells, such as well 72. Each of the wells has a well bottom, such as well bottom 74, which may contact the bottom surface 76 of the mold. Internal structure 78 keeps the microtiter plate centrally positioned with respect to the rest of the mold and any material dispenser positioned above the mold structure. Once pressure is applied, elastomeric seal 80 is sufficiently flexible to allow for vertical or horizontal motion of the outer rim 82 of the plate when the plate is compressed against the substantially planar upper surface 84 of the mold. The position of the center region 86 is maintained by the internal structure. Typically, as a consequence of the movement of the plate, the shape of the elastomeric seal 88 is changed. As illustrated in FIG. 5, the top portion 90 of the elastomeric seal is bent outwardly to a greater extent than before pressure is applied. At this time the plate is precisely aligned with respect to one or more dispensers, or other type of instrument.

Figure 6:
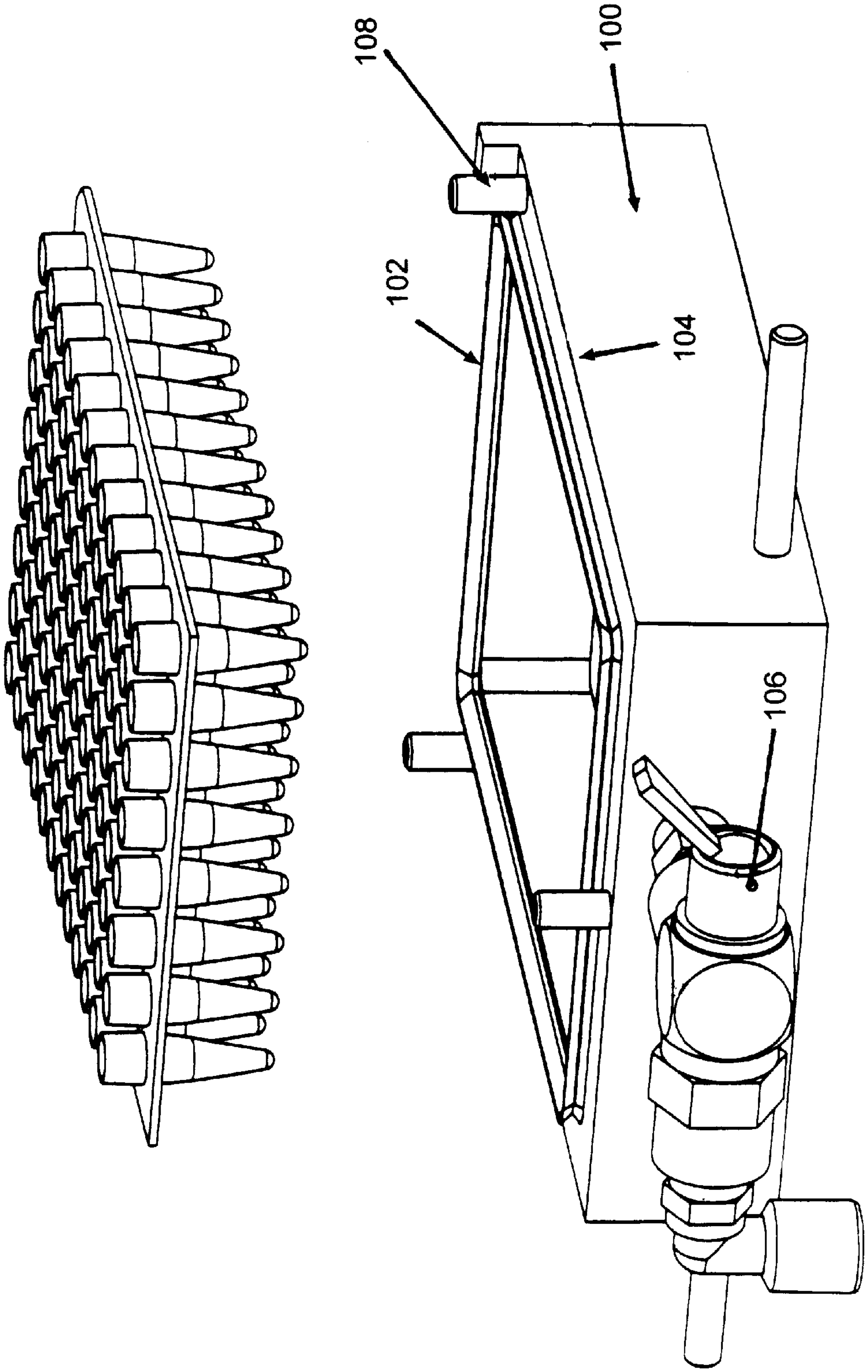
FIG. 6 is a perspective view of a 96-well cycler plate being placed on a mold.

FIG. 6 shows a second embodiment of the invention. FIG. 6 illustrates a mold 100 with an elastomeric seal 102 positioned at the upper surface 104 of the mold. The mold has a vacuum port 106 which can be releasably connected to a vacuum source via an automatically or manually controlled valve. Additionally, the mold may contain a plurality of break structures, such as break structure 108, which are used to limit the closest approach of a dispenser prior to having materials dispensed to or from discrete locations on the work surface of a plate.

Generally, the method is employed for aligning a plate, flattening the work surface of a plate, or equalizing the height of the work surfaces of a plurality of plates for use in automated material transfer procedures. The material transferred may be a detectable (solids, liquids, and the like) or nondetectable (ions, energy and the like) material. The plate may be any composition on which a series of manipulations, including material transfer, is performed. Preferably, the assay plate may be a plate for performing a multiplicity of assays or other laboratory manipulations, such as a 96 or 384-well microtiter plate or cycler plate, or a plate with an even greater number of wells or discrete locations for performing separate assays. Alternatively, the plate may be a glass slide, an array, a microarray, or the like. The dispenser may include liquid dispensing instruments which comprise one or more capillaries, pipette tips, small tubes, printing devices, syringes, closed or open dispensing channels, stamp members and the like. The dispenser may also include ion collection and separation devices (such as capillary electrophoresis columns and related electrodes), mixing probes which transfer mechanical or ultrasonic energy, temperature measurement probes which receive thermal energy levels, conductivity probes, pH probes, solid dispensing devices, and solid phase reactants.

The method may be used to during thermocycling reactions. The method may also be used during biomolecular sequencing reactions for polynucleotides or polypeptides. Alternatively, the method may be used when dispensing materials to discrete locations in a multiple sample assay format, such as for hybridizations or immunoassays. Alternatively, the method may be employed for the mass transfer of materials from one plate to another and where it is desirable that the transfer process be consistent. In yet another alternative, the mold may be employed to support a capillary wash plate which contains liquid for rinsing a material dispenser between two different samples.

In one particular embodiment, a 384-well microtiter plate containing different polynucleotide samples in each well is subjected to a polymerase chain reaction. As a result of the thermocycling reactions, the top surface, or work surface, of the assay plate is no longer of a uniform height. To flatten the work surface of the assay plate again, the microtiter plate is placed on the above-described mold so as to contact the assay plate with the mold-distal end forming an enclosed space bounded by the mold and the assay plate. The internal structure of the support is used to correctly position the assay plate with respect to the mold. Then, a vacuum is pulled through the vacuum port so as to form a seal between the plate and the elastomeric seal and movement of the top portion of the elastomeric seal with respect to the bottom portion occurs. This movement allows for horizontal or lateral motion of the plate with respect to the mold. Once the microtiter plate is correctly positioned further laboratory manipulations may be performed. For example, amplified DNA samples in a microtiter well may be automatically transferred to a microarray printing instrument that aspirate small amounts of liquid and proceed to deposit them on a microarray print station. After transferring liquid from the wells, the microtiter well plate is removed from the mold by releasing the vacuum and removing the plate. At this point a second microtiter plate may be positioned in its place.

It is understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

What is claimed:

1. A method for transferring material to or from discrete locations on a work surface, the method comprising the steps of (a) deforming the work surface to generate a deformed work surface, and (b) transferring material to or from the deformed work surface, wherein the work surface is part of a plate and the deforming step comprises compressing a portion of the plate opposite the work surface against a mold by applying pressure, wherein the plate has an outer rim and the mold comprises:

(c) a bottom surface;

(d) a peripheral wall having a substantially planar upper surface and an elastomeric seal positioned at said upper surface, said peripheral wall positioned to contact the outer rim of the plate, said seal having the necessary flexibility to allow for horizontal or vertical motion of the plate with respect to the mold when pressure is applied; and (e) one or more internal structures for centrally positioning the plate with respect to the mold prior to and during the application of pressure, whereby material transfer is improved.

2. The method of claim 1, wherein the deforming step comprises flattening the work surface.

3. The method of claim 1, wherein the deforming step comprises elongating the work surface.

4. The method of claim 1, wherein the deforming step comprises aligning the work surface with respect to one or more dispensers.

5. The method of claim 1, wherein the deforming step comprises applying positive pressure to the work surface.

6. The method of claim 1, wherein the deforming step comprises applying pressure to the plate opposite the work surface.

7. An automated assay comprising the method of claim 1.

8. A method for automated material transfer to and from discrete locations on the work surface of a plurality of plates, said method comprising:

(a) deforming the work surface of a plate to generate a deformed work surface, whereby the deformed work surface provides improved material transfer;

(b) transferring material to or from the deformed work surface, (c) terminating the deforming step; and (d) repeating steps (a) through (c) using one or more additional plates;

wherein the deforming step further comprises compressing a portion of the plate opposite the work surface against the mold by applying pressure to the plate opposite the work surface, wherein the plate has an outer rim and the mold comprises:

(e) a bottom surface;

(f) a peripheral wall having a substantially planar upper surface and an elastomeric seal positioned at said seal having the necessary flexibility to allow for horizontal or vertical motion of the plate with respect to the mold when pressure is applied for flattening the plate; and (g) one or more internal structures for centrally positioning the plate with respect to the mold prior to and during the application of pressure, whereby material transfer is improved.

9. The method of claim 8, wherein the deforming step comprises flattening the work surface.

10. The method of claim 8, wherein the deforming step comprises elongating the work surface.

11. The method of claim 8, wherein the deforming step comprises applying positive pressure to the work surface.

12. The method of claim 8, wherein the deforming step comprises precisely positioning the work surface of the plate with respect to one or more material dispensers.

* * * * *